(12) United States Patent
Nabutovsky et al.

(10) Patent No.: US 9,895,076 B2
(45) Date of Patent: Feb. 20, 2018

(54) METHOD AND SYSTEM TO DETERMINE CARDIAC CYCLE LENGTH IN CONNECTION WITH CARDIAC MAPPING

(71) Applicant: Pacesetter, Inc., Sunnyvale, CA (US)

(72) Inventors: Yelena Nabutovsky, Mountain View, CA (US); Hoda Razavi, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 211 days.

(21) Appl. No.: 14/703,735

(22) Filed: May 4, 2015

(65) Prior Publication Data

US 2015/0313492 A1 Nov. 5, 2015

Related U.S. Application Data

(60) Provisional application No. 61/988,735, filed on May 5, 2014.

(51) Int. Cl.
| | |
|---|---|
| *A61N 5/04* | (2006.01) |
| *A61B 5/0452* | (2006.01) |
| *A61B 5/04* | (2006.01) |
| *A61B 5/11* | (2006.01) |
| *A61B 5/00* | (2006.01) |
| *A61B 6/00* | (2006.01) |

(52) U.S. Cl.
CPC .......... *A61B 5/0452* (2013.01); *A61B 5/0044* (2013.01); *A61B 5/04012* (2013.01); *A61B 5/1107* (2013.01); *A61B 5/721* (2013.01); *A61B 6/4441* (2013.01)

(58) Field of Classification Search
CPC . A61B 5/1107; A61B 5/0044; A61B 5/04012; A61B 5/0452; A61B 5/721; A61B 5/7232; A61B 5/742; A61B 6/4441
See application file for complete search history.

(56) References Cited

U.S. PATENT DOCUMENTS

| 5,391,199 A | 2/1995 | Ben-Haim |
| 5,713,367 A | 2/1998 | Arnold et al. |
(Continued)

FOREIGN PATENT DOCUMENTS

| EP | 1 070 480 A2 | 1/2001 |
| EP | 1 508 300 A1 | 2/2005 |
(Continued)

OTHER PUBLICATIONS

Notice of Allowance mailed Oct. 27, 2015; Related U.S. Appl. No. 14/328,523.

(Continued)

*Primary Examiner* — Amanda Patton
(74) *Attorney, Agent, or Firm* — Theresa A. Raymer (57) ABSTRACT

A method and system are provided for analyzing data for a region of interest in connection with cardiac mapping. The method and system acquire data recordings of at least one of electrical sensor measurements from an electrical sensor and motion data from a motion sensor in contact with the region of interest, determine cycle lengths associated with cardiac events in the data recordings; and identify a reference cycle length from the cycle lengths determined. The method and system analyze the cycle lengths such that differences in heart rate and cycle length have limited effect on an overall map.

16 Claims, 7 Drawing Sheets

(56) References Cited

U.S. PATENT DOCUMENTS

| | | | |
|---|---|---|---|
| 6,233,476 | B1 | 5/2001 | Strommer et al. |
| 6,301,496 | B1 | 10/2001 | Reisfeld |
| 6,609,027 | B2 | 8/2003 | Kroll et al. |
| 6,633,686 | B1 | 10/2003 | Bakircioglu et al. |
| 6,728,562 | B1 | 4/2004 | Budd et al. |
| 6,751,492 | B2 | 6/2004 | Ben-Haim |
| 6,978,168 | B2 | 12/2005 | Beatty et al. |
| 7,197,354 | B2 | 3/2007 | Sobe |
| 7,263,397 | B2 | 8/2007 | Hauck et al. |
| 7,276,064 | B2 | 10/2007 | Paul et al. |
| 7,338,486 | B2 | 3/2008 | Sliwa et al. |
| 7,386,339 | B2 | 6/2008 | Strommer et al. |
| 7,505,809 | B2 | 3/2009 | Strommer et al. |
| 7,697,973 | B2 | 4/2010 | Strommer et al. |
| 7,881,769 | B2 | 2/2011 | Sobe |
| 8,016,764 | B1 | 9/2011 | Shelchuk |
| 8,195,292 | B2 | 6/2012 | Noren et al. |
| 8,849,381 | B2* | 9/2014 | Lux ..................... A61B 5/0452 600/509 |
| 9,162,067 | B1 | 10/2015 | Farazi et al. |
| 2003/0093067 | A1 | 5/2003 | Panescu |
| 2003/0233039 | A1 | 12/2003 | Shao et al. |
| 2005/0154282 | A1 | 7/2005 | Li et al. |
| 2006/0245536 | A1 | 11/2006 | Boing |
| 2007/0055142 | A1 | 3/2007 | Webler et al. |
| 2007/0073179 | A1 | 3/2007 | Afonso et al. |
| 2007/0100332 | A1 | 5/2007 | Paul et al. |
| 2007/0106146 | A1 | 5/2007 | Altmann et al. |
| 2007/0181139 | A1 | 8/2007 | Hauck |
| 2007/0244479 | A1 | 10/2007 | Beatty et al. |
| 2007/0270705 | A1 | 11/2007 | Starks |
| 2007/0299352 | A1 | 12/2007 | Harlev |
| 2008/0009758 | A1 | 1/2008 | Voth |
| 2008/0091193 | A1 | 4/2008 | Kauphusman et al. |
| 2008/0190438 | A1 | 8/2008 | Harlev |
| 2009/0163904 | A1 | 6/2009 | Miller et al. |
| 2009/0171345 | A1 | 7/2009 | Miller et al. |
| 2009/0275828 | A1 | 11/2009 | Shachar et al. |
| 2009/0306732 | A1 | 12/2009 | Rosenberg |
| 2010/0168550 | A1 | 7/2010 | Byrd et al. |
| 2010/0268059 | A1 | 10/2010 | Ryu |
| 2011/0190593 | A1 | 8/2011 | McNair et al. |
| 2011/0208038 | A1 | 8/2011 | Konofagou et al. |
| 2011/0243401 | A1 | 10/2011 | Zabair et al. |
| 2012/0184863 | A1 | 7/2012 | Harlev et al. |
| 2013/0222415 | A1 | 8/2013 | Vilsmeier |
| 2013/0272592 | A1 | 10/2013 | Eichler et al. |
| 2015/0045867 | A1 | 2/2015 | Krishnan et al. |
| 2015/0133802 | A1 | 5/2015 | Nabutovsky et al. |
| 2015/0141765 | A1 | 5/2015 | Razavi et al. |
| 2015/0141858 | A1 | 5/2015 | Razavi et al. |
| 2017/0042481 | A1 | 2/2017 | Olson |

FOREIGN PATENT DOCUMENTS

| | | |
|---|---|---|
| EP | 2 757 528 A1 | 7/2014 |
| WO | 97/24981 | 7/1997 |
| WO | 2012/090148 A1 | 7/2012 |

OTHER PUBLICATIONS

Notice of Allowance mailed Feb. 25, 2016; Related U.S. Appl. No. 14/328,513.
Notice of Allowance mailed Feb. 25, 2016; Related U.S. Appl. No. 14/703,760.
Non-Final Office Action mailed Mar. 28, 2016; Related U.S. Appl. No. 14/703,749.
Notice of Allowance mailed Apr. 19, 2016; Related U.S. Appl. No. 14/703,181.
USPTO, "Notice of Allowance for U.S. Appl. No. 14/270,176", mailed May 20, 2016.
Notice of Allowance mailed Jun. 22, 2015; Related U.S. Appl. No. 14/328,523.
Bogatyrenko, Evgeniya et al., Efficient Physics-Based Tracking of Heart Surface Motion for Beating Heart Surgery Robotic Systems, International Journal of Computer Assisted Radiology and Surgery, vol. 6, No. 3, pp. 387-399, Aug. 2010.
International Search Report and Written Opinion in PCT Application No. PCT/US2015/028206 (Jul. 22, 2015).
Quatember, Bernhard et al., "Geometric Modeling and Motion Analysis of the Epicardial Surface of the Heart", Mathematics and Computers in Simulation, vol. 81, No. 3, pp. 608-622, Nov. 2010.
Segars, W. Paul et al., "A Realistic Spline-Based Dynamic Heart Phantom", IEEE Transactions on Nuclear Science, vol. 46, No. 3, pp. 503-506, Jun. 1999.
U.S. Appl. No. 09/107,731, filed Jun. 30, 1998 for "Chamber Mapping System".
Advisory Action mailed Aug. 10, 2015; Related U.S. Appl. No. 12/347,216.
Amendment filed Jun. 25, 2015; Related U.S. Appl. No. 12/347,216.
Final Office Action mailed May 4, 2015; Related U.S. Appl. No. 12/347,216.
Amendment filed Dec. 18, 2014: Related U.S. Appl. No. 12/347,216.
Non-Final Office Action mailed Oct. 2, 2014; Related U.S. Appl. No. 12/347,216.
Advisory Action mailed May 1, 2014; Related U.S. Appl. No. 12/347,216.
Amendment filed Apr. 24, 2014; Related U.S. Appl. No. 12/347,216.
Applicant Interview Summary, Apr. 21, 2014; Related U.S. Appl. No. 12/347,216.
Final Office Action mailed Feb. 25, 2014; Related U.S. Appl. No. 12/347,216.
Amendment filed Feb. 4, 2014; Related U.S. Appl. No. 12/347,216.
Non-Final Office Action mailed Nov. 21, 2013; Related U.S. Appl. No. 12/347,216.
Amendment filed Oct. 29, 2012; Related U.S. Appl. No. 12/347,216.
Advisory Action mailed Oct. 11, 2012; Related U.S. Appl. No. 12/347,216.
Amendment filed Oct. 1, 2012; Related U.S. Appl. No. 12/347,216.
Advisory Action mailed Sep. 12, 2012; Related U.S. Appl. No. 12/347,216.
Amendment filed Aug. 28, 2012; Related U.S. Appl. No. 12/347,216.
Final Office Action mailed Jun. 29, 2012; Related U.S. Appl. No. 12/397,216.
Amendment filed May 14, 2012; Related U.S. Appl. No. 12/347,216.
Interview Summary, Feb. 28, 2012; Related U.S. Appl. No. 12/347,216.
Non-Final Office Action mailed Feb. 13, 2012; Related U.S. Appl. No. 12/347,216.
Non-Final Office Action mailed Dec. 11, 2015; Related U.S. Appl. No. 14/703,460.
Non-Final Office Action mailed Sep. 30, 2015; Related U.S. Appl. No. 14/270,181.
Notice of Allowance mailed Dec. 8, 2015; Related U.S. Appl. No. 12/347,216.
Final Office Action mailed Jan. 22, 2016; Related U.S. Appl. No. 14/270,176.
Non-Final Office Action mailed Feb. 8, 2016; Related U.S. Appl. No. 14/270,181.
University of California, SF, "History of AF Ablation", https://cardiology.ucsf.edu/care/clinical/electro/ablation_hist.html, accessed on Jan. 17, 2017.
USPTO, "Final Office Action for U.S. Appl. No. 14/703,749", Date mailed Jan. 23, 2017.
USPTO, "Non-Final Office Action for U.S. Appl. No. 14/270,186", Date mailed Feb. 27, 2017.
USPTO, "Non-Final Office Action for U.S. Appl. No. 14/476,707", Date mailed Mar. 2, 2017.
USPTO, "Non-Final Office Action for U.S. Appl. No. 14/703,744", Date mailed Jan. 13, 2017.

(56) References Cited

OTHER PUBLICATIONS

USPTO, "Non-Final Office Action for U.S. Appl. No. 14/703,757", Date mailed Apr. 6, 2017.
Notice of Allowance dated May 9, 2017; Related U.S. Appl. No. 14/703,749.
St. Jude Medical, "EnSite Velocity Cardiac Mapping System, Model EE3300, v.4" Feb. 28, 2013, 238 pages.
Notice of Allowance dated Jun. 2, 2017; Related U.S. Appl. No. 14/703,744.
Non-Final Office Action dated Jul. 5, 2017; Related U.S. Appl. No. 14/270,191.

* cited by examiner

METHOD AND SYSTEM TO DETERMINE CARDIAC CYCLE LENGTH IN CONNECTION WITH CARDIAC MAPPING

RELATED APPLICATION DATA

The present application relates to and claims priority from the following application: U.S. provisional application Ser. No. 61/988,735, May 5, 2014, titled "METHOD AND SYSTEM TO DETERMINE CARDIAC CYCLE LENGTH IN CONNECTION WITH CARDIAC MAPPING", which is expressly incorporated herein by reference in its entirety in the present application.

BACKGROUND OF THE INVENTION

Embodiments of the present disclosure generally relate to analyzing electrical and mechanical cardiac data and more particularly to determining cardiac cycle length in connection with cardiac mapping.

Current cardiovascular navigation systems, such as the St. Jude Medical MediGuide™ (MDG) cardiovascular navigation system, use fluoroscopic imaging in connection with three dimensional electromagnetic navigation to provide real-time position and orientation of a tool while in a region of interest. The MDG system is integrated with the fluoroscopic imaging system and tracks the sensors continuously within the imaging volume of the fluoroscopic system, on both live fluoroscopy and recorded background.

Cardiac mapping systems, such as the St. Jude Medical Ensite™ Velocity™ Cardiac Mapping System (Ensite), represent established 3-D electroanatomical mapping systems that are used for point-by-point mapping of the electrical state of different cardiac chambers. During a mapping procedure, a roving catheter is moved around a chamber of the heart and electrical activity is measured at each location for a period of time. The procedure is used to characterize the electrical behavior of the cardiac tissue, such as to find areas of low voltage, scar, focal points of arrhythmias, etc.

A need remains for methods and systems that improve the mapping of electrical and mechanical cardiac data.

SUMMARY

In accordance with embodiments herein, methods and systems are provided to analyze electrical and mechanical data such that differences in heart rate and cycle length have a select level (e.g., a minimal) effect on an overall map created from electrical and motion data. In accordance with embodiments herein, methods and systems are provided to analyze motion and electrical data prospectively and retrospectively. In accordance with embodiments herein, methods and systems are provided to minimize recording length during a procedure to collect and analyze motion and electrical data.

In accordance with embodiments herein, methods and systems are provided to analyze data of a region of interest in connection with cardiac mapping. The methods and systems acquire data recordings of at least one of electrical sensor measurements from an electrical sensor, and motion data from a motion sensor, in contact with the region of interest. The methods and systems determine cycle lengths (CLs) associated with cardiac events in the data recordings; and identify a reference cycle length from the cycle lengths determined.

Optionally, the methods and systems analyze the cycle lengths such that differences in heart rate and cycle length have limited effect on an overall map. Optionally, the methods and systems further comprise minimizing data recording length during a mapping procedure. Optionally, the methods and systems further comprise providing assistance indicia to a user indicative of a suggested beat to choose for the reference cycle length. Optionally, the methods and systems find statistical information that describes CLs in at least a portion of the data recordings.

DETAILED DESCRIPTION

The description that follows sets forth one or more illustrative embodiments. It will be apparent that the teachings herein may be embodied in a wide variety of forms, some of which may appear to be quite different from those of the disclosed embodiments. Consequently, the specific structural and functional details disclosed herein are merely representative and do not limit the scope of the disclosure. For example, based on the teachings herein one skilled in the art should appreciate that the various structural and functional details disclosed herein may be incorporated in an embodiment independently of any other structural or functional details. Thus, an apparatus may be implemented or a method practiced using any number of the structural or functional details set forth in any disclosed embodiment(s). Also, an apparatus may be implemented or a method practiced using other structural or functional details in addition to or other than the structural or functional details set forth in any disclosed embodiment(s).

Throughout the present disclosure, the terms beat, cardiac cycle, event and cardiac event are used interchangeably to refer to a single complete cardiac cycle of the heart, such as from the cycle beginning at the start of an intrinsic or paced atrial event (e.g., the P-wave) and continuing until the beginning of the next intrinsic or paced atrial event (e.g., next P-wave).

Embodiments herein may be implemented with, and/or utilize aspects of, the methods and system described in the following applications:

U.S. patent application Ser. No. 14/328,523, filed Jul. 10, 2014, titled "METHOD AND SYSTEM TO ASSESS MECHANICAL DYSSYNCHRONY BASED ON MOTION DATA COLLECTED BY A NAVIGATION SYSTEM", now U.S. Pat. No. 9,301,713, U.S. patent application Ser. No. 14/328,513, filed Jul. 10, 2014, titled "METHOD AND SYSTEM TO MEASURE CARDIAC MOTION USING A CARDIOVASCULAR NAVIGATION SYSTEM", now U.S. Pat. No. 9,314,191, U.S. Pub. No. 2015/0141765, filed Sep. 5, 2014, titled "METHOD AND SYSTEM TO IDENTIFY MOTION DATA ASSOCIATED WITH CONSISTENT ELECTRICAL AND MECHANICAL BEHAVIOR FOR A REGION OF INTEREST", U.S. patent application 61/988,779, filed May 5, 2014, titled "METHODS AND SYSTEMS TO CALCULATE TIME OF MECHANICAL ACTIVATION USING CHARACTERICATION MOTION DATA AREA STRAINS", U.S. patent application Ser. No. 14/270,181, filed May 5, 2014, titled "METHOD AND SYSTEM TO CHARACTERIZE MOTION DATA BASED ON NEIGHBORING MAP POINTS", now U.S. Pat. No. 9,364,170, U.S. Pub. No. 2015/0313480, filed May 5, 2014, titled "METHOD AND SYSTEM FOR CALCULATING STRAIN FROM CHARACTERIZATION DATA OF A CARDIAC CHAMBER", U.S. patent application Ser. No. 14/270,176, filed May 5, 2014, titled "METHOD AND SYSTEM FOR DISPLAYING A THREE DIMENSIONAL VISUALIZATION OF CARDIAC MOTION", now U.S. Pat. No. 9,380,940, U.S. patent application 61/988,763, filed May 5, 2014, titled "METHOD AND SYSTEM TO EQUALIZING CARDIAC CYCLE LENGTH BETWEEN MAP POINTS", U.S. patent application 61/988,767, filed May 5, 2014, titled "METHOD AND SYSTEM TO SUBDIVIDE A MAPPING AREA FOR MECHANICAL ACTIVATION ANALYSIS", U.S. patent application 61/988,771, filed May 5, 2014, titled "CARDIAC RESYNCHRONIZATION SYSTEM AND METHOD", and U.S. patent application 61/988,774, filed May 5, 2014, titled "SYSTEM AND METHOD FOR EVALUATING LEAD STABILITY OF AN IMPLANTABLE MEDICAL DEVICE".

All of the above cited applications are expressly incorporated herein by reference in their entirety.

Figure 1:
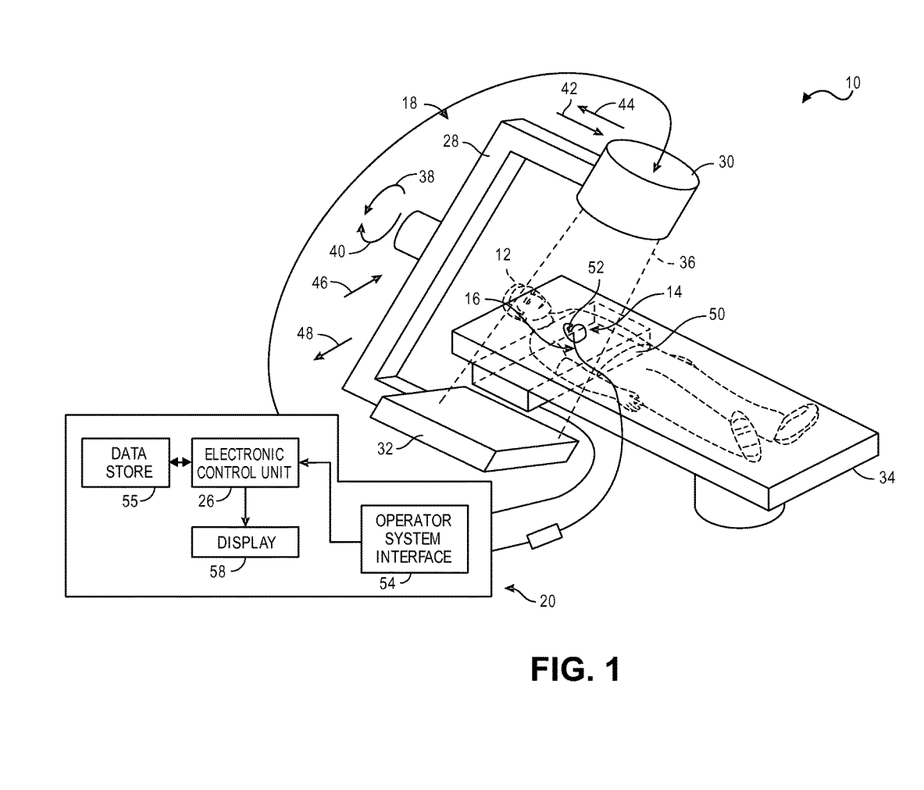
FIG. 1 illustrates an imaging and navigation system of an embodiment.

FIG. 1 illustrates a cardiovascular navigation system 10, of an embodiment, for use in imaging an anatomical region of a patient 12 such as a heart 14. A medical tool 16 is placed within the anatomical region, such as for example, an electrophysiological (EP) mapping catheter or a catheter generally described or shown in U.S. Pat. No. 7,881,769, the entire disclosure of which is incorporated herein by reference. The medical tool 16 includes a plurality of electrophysiological sensors 52 that may be placed on the endocardial or epicardial surface of the left ventricle of the heart 14. The electrophysiological sensors 52 may be attached to the distal or proximal end of the medical tool 16, or any point in between. The electrophysiological sensors 52 measure a position and an electrical potential or electric current of biological cells and tissues, and are transmitted to an electronic control unit (ECU) 26. For example, the electrophysiological sensors 52 may be positioned by the medical tool 16 to measure the electrical potential along a portion of the wall of the heart 14. It should be understood, however, that the electrophysiological sensors 52 could be used in a variety of anatomical regions within the heart 14 or other organs in which motion characterization may be of interest. Additionally or alternatively, the electrophysiological sensors 52 may be replaced by separate motion sensors and electrical sensors. The motion sensors in contact with the region of interest measuring the position and electrical sensors measuring the electrical potential or electric current of the region of interest. Optionally, ECU 26 may receive the position and electrical sensor measurements simultaneously from the motion sensors and electrical sensors.

System 10 may include an imaging system 18 and a medical device mapping system 20. The system 10 may also include a registration system for registering a group of images of the anatomical region of patient 12 in a navigation coordinate system of the mapping system 20 as generally described and shown in U.S. Patent Publication 2013/0272592 and International Pub. No. WO 2012090148, each of which is entirely incorporated herein by reference.

The imaging system 18 may be provided to acquire images of heart 14 or another anatomical region of interest and comprises a fluoroscopic imaging system in the illustrated embodiment. Additionally or alternatively, rather than a fluoroscopic imaging system, a computed tomography (CT) imaging systems, three-dimensional radio angiography (3DRA) systems and the like may be used. Although the imaging system 18 is described herein for an embodiment of the invention, the imaging system 18 is not required for the inventive subject matter described within this application.

The imaging system 18 may include a C-arm support structure 28, a radiation emitter 30, and a radiation detector 32. Emitter 30 and detector 32 are disposed on opposite ends of support structure 28 and disposed on opposite sides of patient 12 as patient 12 lays on an operation table 34. Emitter 30 and detector 32 define a field of view 36 and are positioned such that the field of view 36 includes the anatomical region of interest as patient 12 lays on operation table 34. Imaging system 18 is configured to capture images of anatomical features and other objects within field of view 36. The C-arm support structure 28 may have freedom to rotate about the patient as shown by lines 38, 40. The C-arm support structure 28 may also have freedom to slide along lines 42, 44 (i.e. along the cranio-caudal axis of patient 12) and/or along lines 46, 48 (i.e. perpendicular to the cranio-caudal axis of patient 12). Rotational and translational movement of support structure 28 yields corresponding rotational and translational movement of field of view 36.

Imaging system 18 may acquire a group of images of an anatomical region of patient 12 by first shifting along lines 42, 44, 46, 48 to place the anatomical region of interest within the field of view 36. Second, the C-arm support structure 28 may rotate radiation emitter 30 and radiation detector 32 about patient 12, keeping the anatomical region within field of view 36. Imaging system 18 may capture images of the anatomical region as support structure 28 rotates, providing a group of two-dimensional images of the anatomical region from a variety of angles. The group of images may be communicated to ECU 26 for image processing and display. The group of images may comprise a sequence of images taken over a predetermined time period.

The mapping system 20 may be provided to determine the position and orientation of medical tool 16 within the body of patient 12 and to permit a clinician to navigate the medical tool 16 within the body. In the illustrated embodiment, system 20 comprises a magnetic navigation system in which magnetic fields are generated in the anatomical region and position sensors associated with tool 16 generate an output that changes responsive to the position of the sensors within the magnetic field. System 20 may comprise, for example, the systems generally shown and described in, for example, U.S. Pat. Nos. 6,233,476, 7,197,354, 7,386,339, and 7,505,809 all of which are incorporated by reference in their entirety. Although a magnetic navigation system is shown in the illustrated embodiment, it should be understood that the invention could find use with a variety of navigation systems including those based on the creation and detection of axes specific electric fields. The mapping system 20 may include a transmitter assembly 50.

The transmitter assembly 50 is conventional in the art and may include a plurality of coils arranged orthogonally to one another to produce a magnetic field in and/or around the anatomical region of interest. It should be noted that, although transmitter assembly 50 is shown under the body of patient 12 and under table 34 in FIG. 1, transmitter assembly 50 may be placed in another location, such as attached to radiation emitter 30, from which the magnetic field generators can project a magnetic field in the anatomical region of interest. In accordance with certain embodiments of the invention the transmitter assembly 50 is within the field of view 36. The ECU 26 may control the generation of magnetic fields by transmitter assembly 50.

The electrophysiological sensors 52 are configured to generate an output dependent on the relative position of electrophysiological sensors 52 within the field generated by transmitter assembly 50. In FIG. 1, the electrophysiological sensor 52 and medical tool 16 are shown disposed around the heart 14. As medical tool 16 is guided to and through the region of interest, the mapping system 20 determines the location of the electrophysiological sensors 52 in the generated field, and thus the position of medical tool 16 as well. The mapping system 20 further determines a navigation coordinate such as a cartesian coordinate (e.g., (X, Y, Z)), of the navigation coordinate system.

One or more patient reference sensors (not shown) are on the body of the patient 12, for example, on the chest. The patient reference sensors (PRS) measure a displacement and orientation of the patient reference sensors relative to a predetermined reference point, such as, the electrophysiological sensors 52 or the transmitter assembly 50.

The ECU 26 of the mapping system 20 may include or represent hardware circuits or circuitry that include and/or are connected with one or more logic based devices, such as processors, microprocessors, controllers, microcontrollers, or other logic based devices (and/or associated hardware, circuitry, and/or software stored on a tangible and non-transitory computer readable medium or memory). The ECU 26 may receive a plurality of input signals including signals generated by medical tool 16, imaging system 18, the electrophysiological sensors 52, an operator system interface 54, and the patient reference sensors and generate a plurality of output signals including those used to control tool 16, imaging system 18, the display 58. The operator system interface 54 may include a keyboard, a keypad, buttons, a touchscreen, a monitor, a mouse, and the like. ECU 26 may also receive an input signal from an organ monitor (not shown), such as an ECG monitor, and sort or segregate images from imaging system 18 based on a timing signal of a monitored organ. For example, ECU 26 may sort images based on the phase of the patient's cardiac cycle at which each image was collected, as more fully described in U.S. Pat. No. 7,697,973, which is hereby incorporated by reference in its entirety.

The mapping system 20 includes a data store 55 to store, among other things, the original/raw motion data, the original electrical sensor measurements, modified motion data, modified sensor measurements, as well as instructions to direct one or more processors to perform the operations described herein.

The methods described herein may be implemented as a software algorithm, package, or system that directs one or more hardware circuits or circuitry to perform the actions described herein. For example, the operations of the methods may represent actions to be performed by one or more circuits that include or are connected with processors, microprocessors, controllers, microcontrollers, Application Specific Integrated Circuits (ASICs), Field-Programmable Gate Arrays (FPGAs), or other logic-based devices that operate using instructions stored on a tangible and non-transitory computer readable medium (e.g., a computer hard drive, ROM, RAM, EEPROM, flash drive, or the like), such as software, and/or that operate based on instructions that are hardwired into the logic of the.

Motion mapping refers to the use of the mapping system in which a map-enabled catheter is moved around an anatomical structure and the 3-D position is recorded for a period of time (i.e. 30 seconds) at each location. Motion can then be characterized by analyzing movement of the various MDG map points in relation to each other. The map-enabled catheter may be moved around the entire LV endocardium, in order that movement of the entire LV may be assessed. Alternatively or additionally, the map-enabled catheter may be inserted into veins that are candidates for LV lead placement. Movement of the portion of the LV spanned by these veins can then be assessed. However, it is to be understood that the present disclosure is not limited to use with electrical/motion data collected by an mapping system, but instead embodiments of the present disclosure may be used with any system that is able to collect electrical/motion data at map points across the surface of the heart (endocardial and/or epicardial).

The systems noted above utilize measurements of the time of local electrical or mechanical activation by considering individual beats at each map point. For example, the cardiac mapping system may buffer ten or more cardiac beats and allow the user to choose one of the ten or more beats for mapping. However, when the user is choosing the beat, the user may not have a global view into the beats at the other map points. During a mapping procedure, there may be large variability in cycle lengths (CL) between consecutive beats in a recording at each map point as well as variability in CLs between different map points. This variability may be introduced by different sedation states of the patient or administration of various drugs during the procedure. Small variability in CL mostly affects the diastolic portion of the cardiac cycle. However, as the CL gets shorter and shorter, the systolic portion can also become altered.

In accordance with embodiments herein, for accurate mapping, it is desirable to use beats from different map points that have similar CLs to maintain homogenous mechanical and electrical loading. Embodiments of the methods and systems herein automatically choose a single beat with an appropriate CL from each map point, both prospectively during the data collection stage and retrospectively, to build a final map.

During electrical and mechanical data collection, data recordings are made for several map points in the heart and stored in the data store 55. Each data recording lasts for some select period of time (i.e. 30 seconds) and includes electrical/motion data collected in connection with multiple heart beats, the number depending on the heart rate. The heart rate may vary within each recording and between recordings. In accordance with embodiments herein, a retrospective method identifies a cycle length (CL) that a select number of map points (e.g. a majority, most) shares and chooses a particular beat (or set of beats) associated with each map point to use for analysis such that differences in CL will have limited (e.g., minimal) impact on the analysis. The retrospective analysis may be implemented when it is acceptable to collect all of the data first and then interpret the data after collection. By way of example only, a retrospective analysis may be performed during a clinical trial or when seeking to implement a control process that cycles through various parameters and then compare the results to arrive at select parameter settings. A retrospective analysis method is described in connection with FIGS. 2 and 3.

In accordance with embodiments herein, a prospective method is provided for performing data collection that seeks to limit (e.g., minimize) the data collection time based on the presence of a beat with the desired CL. The prospective analysis may be used on a point-by-point basis during a mapping procedure. Embodiments of the methods and systems described herein may be used during prospective analysis because the methods and systems may reduce the length of a recording taken at each map point and may reduce or eliminate the need for a user to manually choose a particular beat. Prospective analyses methods are described in connection with FIGS. 4 and 5.

The processes described in connection with FIGS. 2-5 are implemented by one or more processors, such as by the ECU 26, external device 600 (FIG. 6) or within another computer system.

Figure 2:
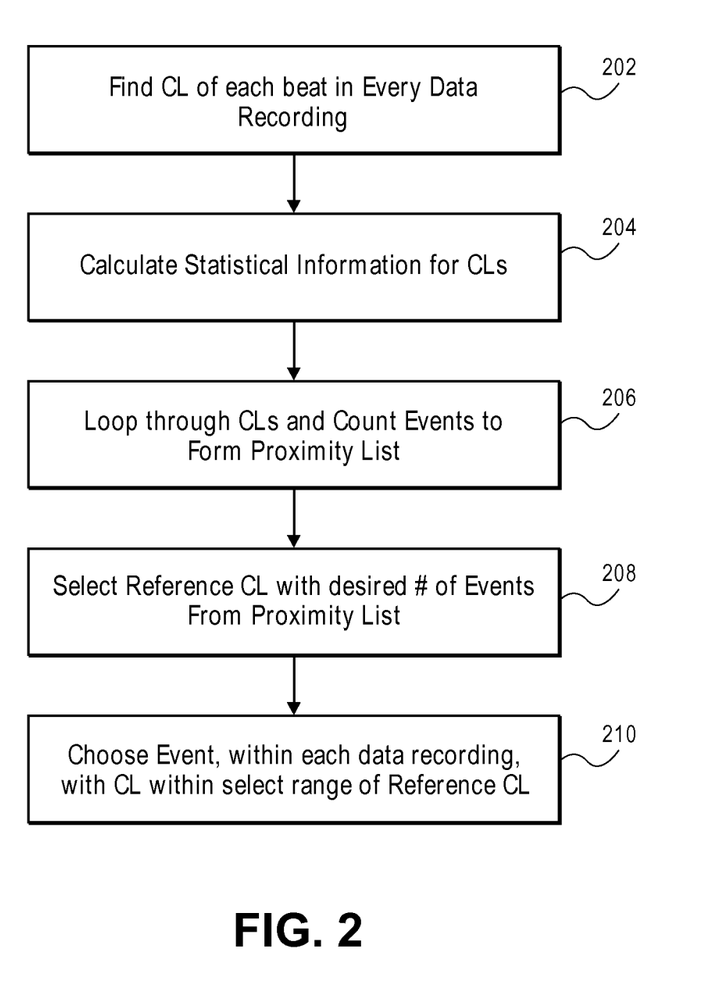
FIG. 2 illustrates a process for performing a retrospective analysis of data after a data recording has been collected in accordance with an embodiment.
Figure 3A:
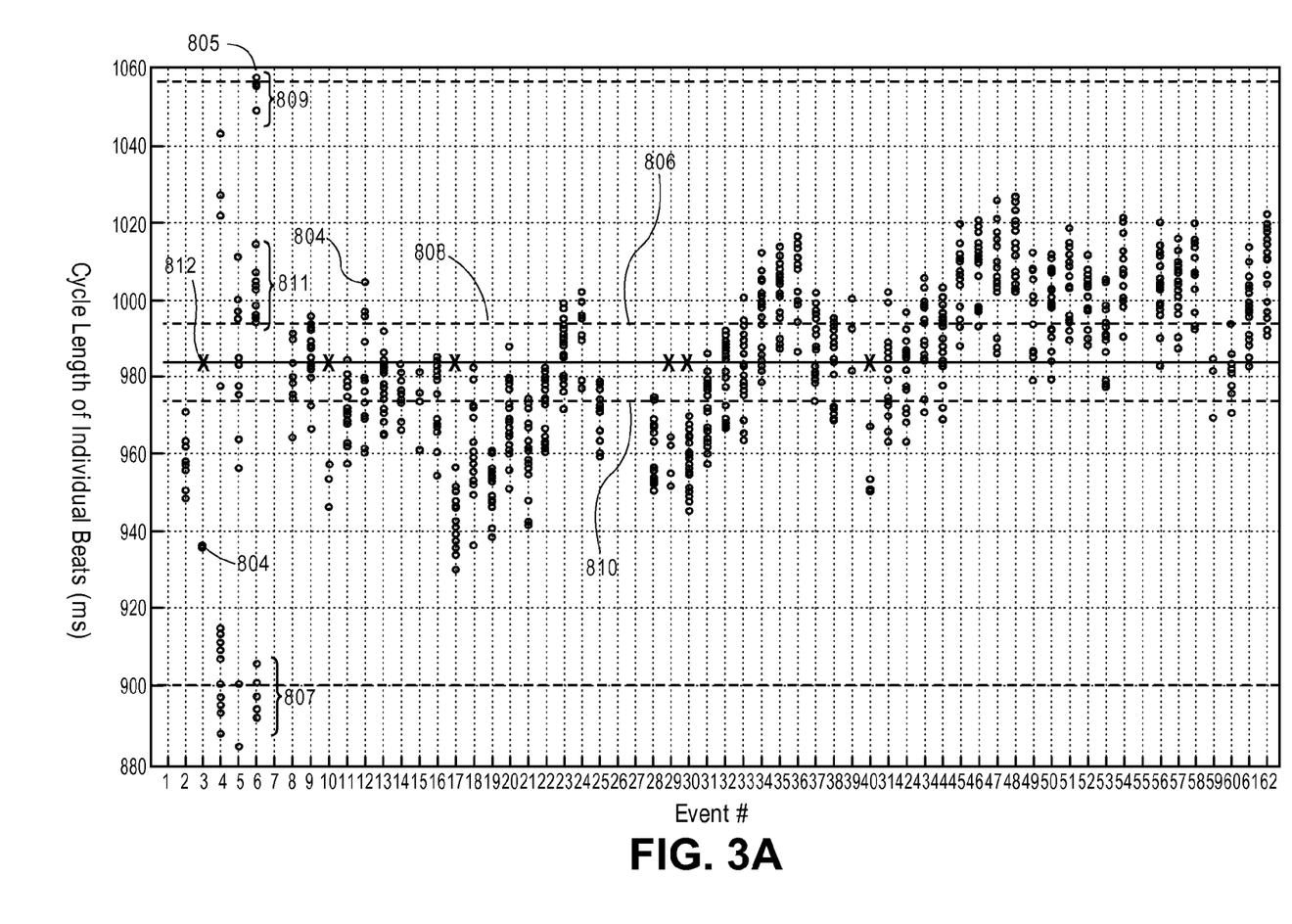
FIG. 3A illustrates an example of a CL data set that may be created when implementing the process of FIG. 2 in connection with a patient having atrial fibrillation who is currently in sinus rhythm in accordance with an embodiment.
Figure 3B:
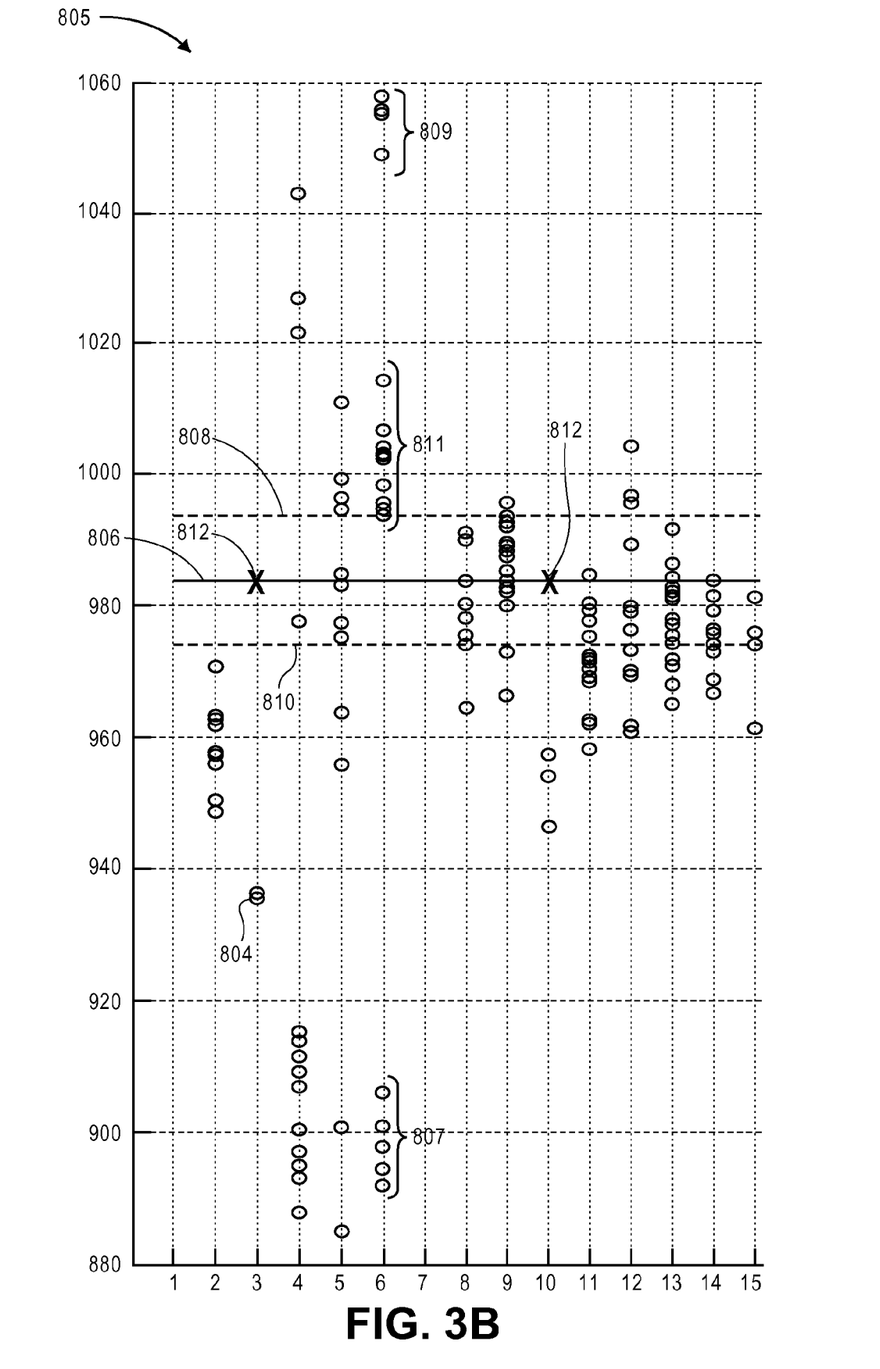
FIG. 3B illustrates an expanded view of the first 15 data recordings from FIG. 3A, for better clarity in accordance with an embodiment.

FIG. 2 illustrates a process for performing a retrospective analysis of data after a data recording has been collected. For example, the data recording may comprise electrical/motion data collected from a corresponding map point over multiple cardiac cycles (e.g., beats), such as over 20, 30 or more than 30 cardiac cycles/beats. The process of FIG. 2 automatically selects one or more cardiac cycles/beats from each data recording (out of a group of data recordings) that are of interest for use in the combined analysis.

At 202, the method finds the cycle length (CL) of each beat in each data recording. The CL for a corresponding cardiac event is determined based on the time difference between successive occurrences of a characteristic of interest (e.g., the P-wave, T-wave, R-wave) in the successive cardiac events. For example, the CL may correspond to the time difference between the peak of the R-wave (or any other reference signal) in the current cardiac event and the peak of the R-wave in the next cardiac event.

At 204, the method finds statistical information that describes the CLs in at least a portion or all of the data recordings. For example, the method may find a minimum, maximum, and mean, as the statistical information, for a portion or all of the CLs in some or all of the data recordings.

At 206, the method loops through a select set or all possible CLs starting with the cardiac event having the minimum CL and going to the maximum CL in set steps (i.e. 5 ms). The method obtains a current test CL (from a current data recording) and compares the current test CL to each CL within an overall collection of CLs. The overall collection of CLs may represent a complete set of CLs for an overall collection (or a select partial set of) of cardiac events that are in an overall collection (or a select partial set) of data recordings. For each current test CL, the method counts how many CLs from the overall collection of CLs fall within select upper and lower thresholds (i.e. ±10 ms) of the current test CL. The count results in a determination of a number of cardiac events that have CLs within upper and lower thresholds of the current test CL being analyzed. Each count is saved, as a proximity count, in connection with the corresponding CL. The operation at 206 is repeated for multiple CL (e.g., all CL or a select portion of the overall collection of CL). The method saves the proximity counts as a proximity list, where the proximity list includes, for each test CL, a proximity count of cardiac events having a CL within the thresholds of the corresponding test CL.

At 208, the method analyzes the proximity list and chooses a reference CL from the proximity list. The reference CL has a desired number (e.g. the most) of cardiac events within the corresponding upper and lower limits. By way of example, the reference CL may represent an optimal CL to be used for subsequent processing and analysis. Optionally, when more than one CL fits the criteria applied at 208, the method may choose, as the reference CL, the CL that is closest to the mean of the collection of CLs.

At 210, the method chooses (for analysis) the cardiac event (e.g. beat) within each data recording, that has an associated CL that is within a select range of the reference CL (e.g., closest to the reference CL).

Optionally, if a data recording does not have a CL within some threshold (i.e. 20 ms) of the reference CL, the method may eliminate the data recording from the analysis. If this results in elimination of too many data recordings, the method may repeat the analysis and utilize a larger tolerance, thereby reducing the number of data recordings that are eliminated.

FIG. 3A illustrates an example of a CL data set that may be created when implementing the process of FIG. 2 in connection with a patient having atrial fibrillation who is currently in sinus rhythm. FIG. 3B illustrates an expanded view of the first 15 data recordings from FIG. 3A, for better clarity. In FIGS. 3A and 3B, the horizontal axis corresponds to individual data recordings (denoted #1-#62), while each vertical column corresponds to the cycle length of individual beats or cardiac events recorded during the corresponding data recording. In the example of FIGS. 3A and 3B, the vertical column illustrates cycle lengths between 880 ms and 1060 ms. Each cardiac cycle has a corresponding cycle length that is indicated along the vertical column as a circle 804.

With reference to FIG. 3B, the data recording #6 includes approximately 15 cardiac events/beats along the vertical line 805, where five cardiac events/beats have CLs between 890-910 ms at cluster 807, three cardiac events/beats have CLs above 1050 ms at cluster 809 and seven CLs are between 990-1015 ms at cluster 811. The horizontal solid line 806 represents the reference (e.g., optimal) CL chosen based on the process of FIG. 2. The horizontal dashed lines 808, 810 represent the upper and lower thresholds used at 206 to count the number of cardiac events within the thresholds of a particular current CL. The crosses 812 denote data recordings that do not have any beats with a CL that satisfied the CL criteria, namely that do not have a CL between thresholds 808, 810.

Figure 4:
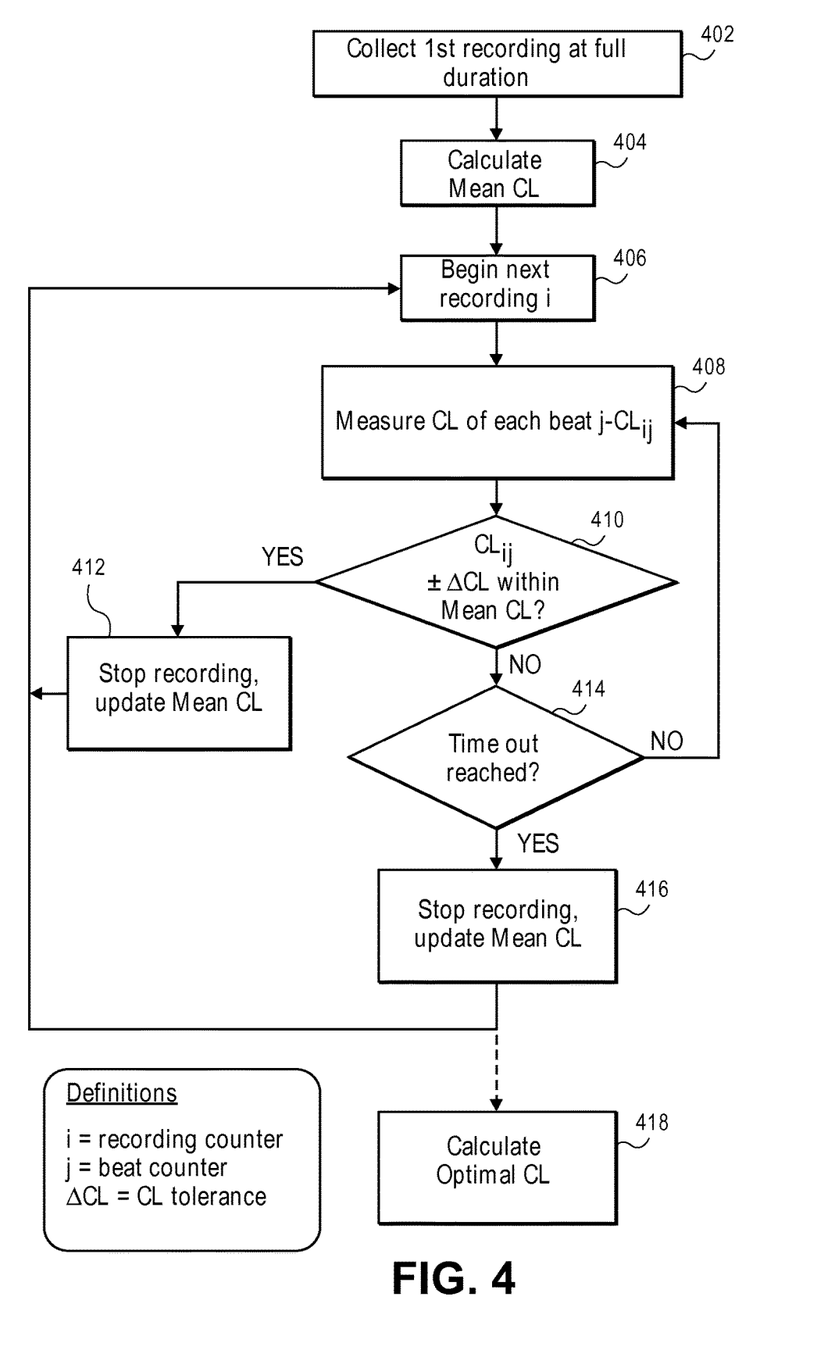
FIG. 4 illustrates a process for performing a prospective analysis of a data recording while the data recording is being collected based on a mean CL in accordance with an embodiment.

FIG. 4 illustrates a process for performing a prospective analysis of a data recording while the data recording is being collected based on a mean CL. At 402, the method collects a first or base data recording over a single data recording duration. For example, a single data recording duration may be up to 20 seconds, 10-30 seconds or longer.

At 404, the method determines the cycle length for the electrical/motion data collected during each cardiac event in a single data recording. At 404, the method calculates the mean of the CLs in the first or base data recording (CLmean) to form a base CL. Optionally, the method may calculate another statistical parameter, other than mean, as the base CL for the CLs in the base data recording.

At 406, the method begins to collect electrical/motion data for the next data recording. Throughout the duration of collecting electrical/motion data in connection with the next data recording, the method performs the operations at 406 to 414. At 408, the CL for a current cardiac cycle is measured. At 410, the method determines whether the CL for the current cardiac cycle is within the upper and lower thresholds of the CL mean. When the current CL is within the upper and lower thresholds, flow moves to 412. Otherwise flow moves to 414.

At 412, the method stops collecting electrical/motion data for the data recording and recalculates/updates the base CL (e.g. CLmean) based on a select portion or all of the CLs in base and additional data recordings.

At 414, the method determines whether the time period for collecting electrical/motion data for the associated data recording has timed out. When the time period for the associated data recording times out, flow moves to 416. Otherwise, flow moves returns to 408 where the CL is measured for the next cardiac cycle/beat.

When the time period times out at 414, flow moves to 416 where the process stops recording electrical/motion data for the current data recording. At 416, the process also updates the base/mean CL for the current data recording. Next, flow returns to 406 and the operations at 406 to 416 are repeated for the next data recording in connection with the next map point. The operations at 406 to 416 are repeated at each map point.

The iterative operations at 406 to 416 may also continue as long as the clinical circumstances allow. For example, the electrical/motion data may be collected for the next data recording until the mapping tool moves, until contact is lost between the mapping tool and the surface of the tissue, or a certain amount of time has passed.

Once data recordings for all map points have been collected, the process moves to 418 wherein a retrospective analysis is performed to choose a reference CL (e.g. the optimal CL) for the final map and re-assign beats to earlier beats if appropriate.

Figure 5:
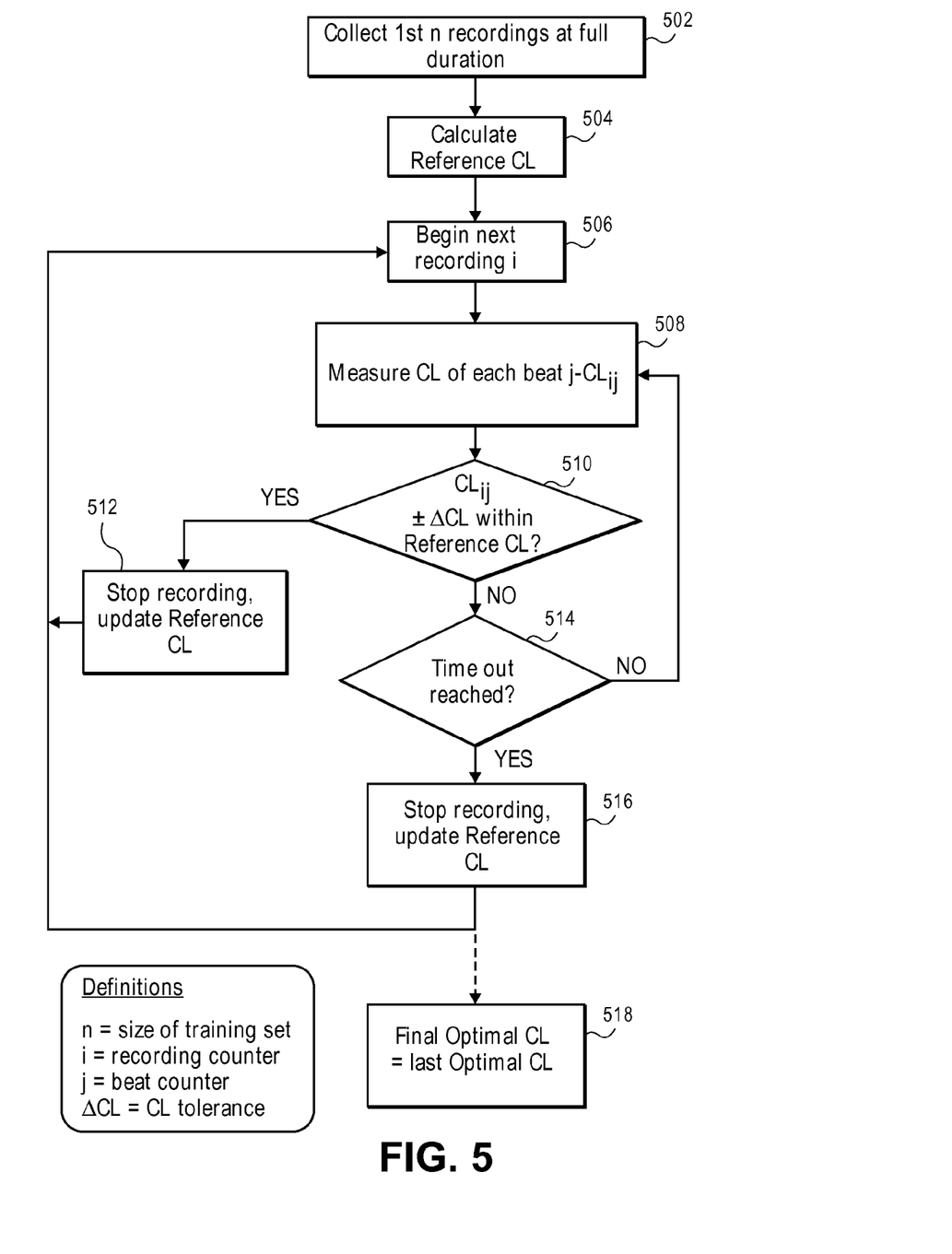
FIG. 5 illustrates a process for performing a prospective analysis of a data recording while the data recording is being collected based on a frequent CL (e.g., the most frequent CL) in accordance with an embodiment.

FIG. 5 illustrates a process for performing a prospective analysis of a data recording while the data recording is being collected based on a frequent CL (e.g., the most frequent CL). At 502, the method collects one or more base data recordings over one or more data recordings that act as a training set. For example, one, five, or ten data recordings may be collected at 502.

At 504, the method determines the cycle length for the electrical/motion data collected during each cardiac event in the training set of data recordings. For example, the process of FIG. 2 may be applied to the training set of data recordings to calculate a preliminary reference CL. For example, at 504, the method may calculate the CL that occurs with a select frequency base reference CL.

At 506, the method begins to collect electrical/motion data for the next data recording. Throughout the duration of collecting electrical/motion data in connection with the next data recording, the method performs the operations at 506 to 514. At 508, the CL for a current cardiac cycle is measured.

At 510, the method determines whether the CL for the current cardiac cycle is within the upper and lower thresholds of the base/reference CL. When the current CL is within the upper and lower thresholds, flow moves to 512. Otherwise flow moves to 514.

At 512, the method stops collecting electrical/motion data for the data recording and recalculates/updates the base reference CL (e.g. the most frequent CL) based on a select portion or all of the CLs in the base and additional data recordings.

At 514, the method determines whether the time period for collection electrical/motion data for the associated data recording has timed out. When the time limit for the associated data recording times out, flow moves to 516. Otherwise, flow moves returns to 508 where the CL is measured for the next cardiac cycle/beat.

When the timer times out at 514, flow moves to 516 where the process stops recording electrical/motion data for the current data recording. At 516, the process also updates the base/reference CL for the current data recording. Next flow returns to 506 and the operations at 506 to 516 are repeated for the next data recording in connection with the next map point. The operations at 506 to 516 are repeated at each map point.

The iterative operations at 506 to 516 may also continue as long as the clinical circumstances allow. For example, the electrical/motion data may be collected for the next data recording until the mapping tool moves, until contact is lost between the mapping tool and the surface of the tissue, or a certain amount of time has passed.

Once data recordings for all map points have been collected, the process moves to 518 wherein a retrospective analysis is performed to choose a reference CL (e.g. the optimal CL) for the final map.

Figure 6:
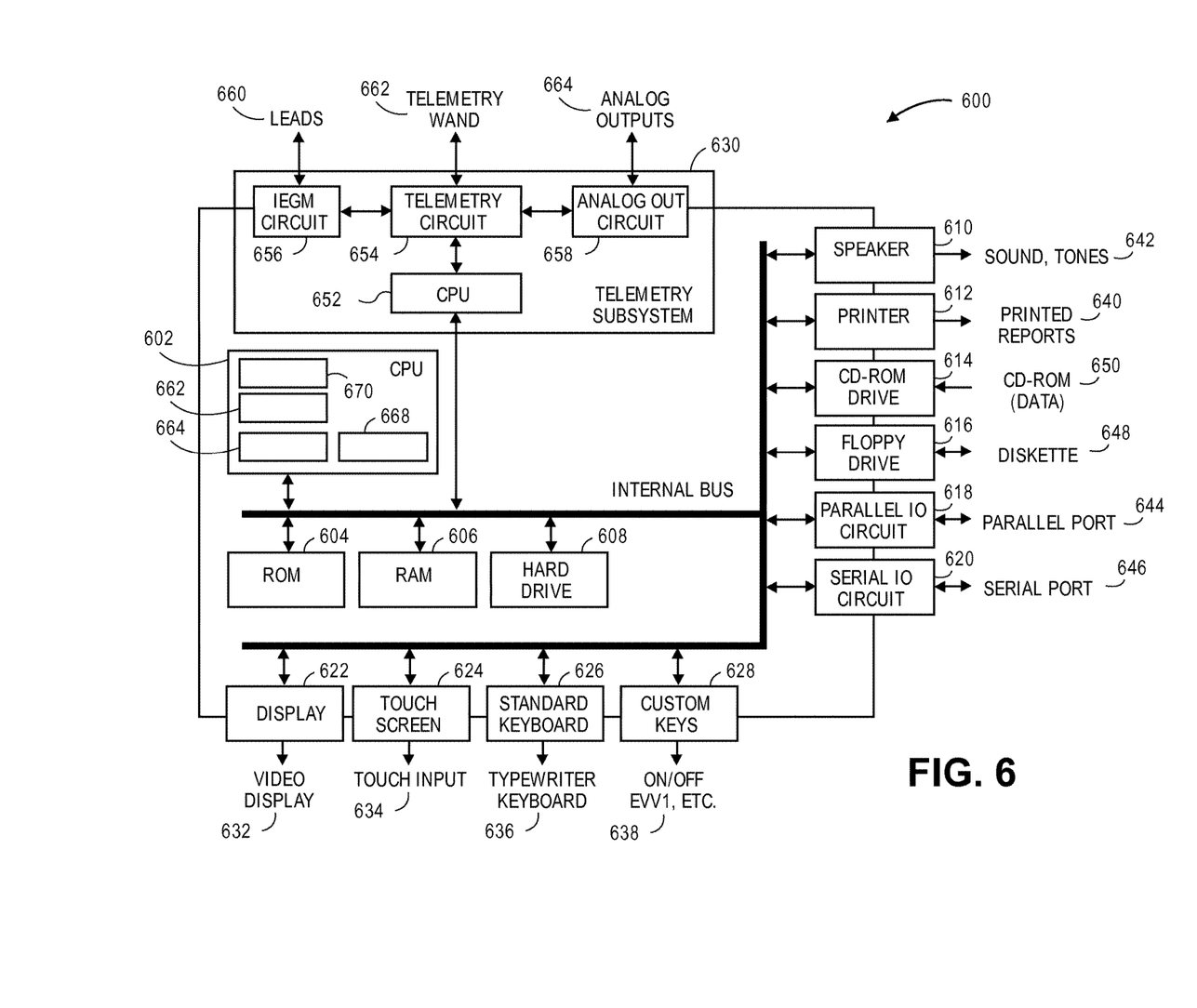
FIG. 6 illustrates a functional block diagram of an external device 600 that is operated in accordance with the processes described herein to analyze motion and electrical data and to interface with implantable medical devices (IMD).

FIG. 6 illustrates a functional block diagram of an external device 600 that is operated in accordance with the processes described herein to analyze motion and electrical data and to interface with implantable medical devices (IMD). The external device 600 may be a workstation, a portable computer, an IMD programmer, a PDA, a cell phone and the like. The external device 600 includes an internal bus that connects/interfaces with a Central Processing Unit (CPU) 602, ROM 604, RAM 606, a hard drive 608, the speaker 610, a printer 612, a CD-ROM drive 614, a floppy drive 616, a parallel I/O circuit 618, a serial I/O circuit 620, the display 622, a touch screen 624, a standard keyboard connection 626, custom keys 628, and a telemetry subsystem 630. The internal bus is an address/data bus that transfers information between the various components described herein. The hard drive 608 may store operational programs as well as data, such as waveform templates and detection thresholds.

The CPU 602 typically includes a microprocessor, a microcontroller, or equivalent control circuitry, designed specifically to control interfacing with the external device 600 and with the IMD. The CPU 602 performs the processes discussed above. The CPU 602 may include RAM or ROM memory, logic and timing circuitry, state machine circuitry, and I/O circuitry to interface with the IMD. The display 622 (e.g., may be connected to the video display 632). The touch screen 624 may display graphic information relating to the IMD. The display 622 displays various information related to the processes described herein. The touch screen 624 accepts a user's touch input 634 when selections are made. The keyboard 626 (e.g., a typewriter keyboard 636) allows the user to enter data to the displayed fields, as well as interface with the telemetry subsystem 630. Furthermore, custom keys 628 turn on/off 638 (e.g., EVVI) the external device 600. The printer 612 prints copies of reports 640 for a physician to review or to be placed in a patient file, and speaker 610 provides an audible warning (e.g., sounds and tones 642) to the user. The parallel I/O circuit 618 interfaces with a parallel port 644. The serial I/O circuit 620 interfaces with a serial port 646. The floppy drive 616 accepts diskettes 648. Optionally, the floppy drive 616 may include a USB port or other interface capable of communicating with a USB device such as a memory stick. The CD-ROM drive 614 accepts CD ROMs 650.

The CPU 602 is configured to analyze motion data and electrical measurement data collected by the cardiovascular navigation system and perform the prospective and retrospective analysis of cycle lengths as discussed herein.

The CPU 602 receives access to electrical/motion data (MD) sets, as explained herein and performs various analysis prior to, or after, the cycle length analysis discussed above in connection with FIGS. 2-5. For example, The CPU 602 may include an SSMD subset analysis circuit module 662 that divides the SSMD subsets of data into quadrants associated with corresponding phases of the cardiac cycle with raw electrical and motion data. For example, the CPU 602 may include an electrical waveform analysis circuit module 664 that analyzes the electrical sensor measurements of the heart. The electrical waveform analysis circuit module 664 analyzes the electrical sensor measurements to locate ectopic beats within the electrical sensor measurement data. Once an ectopic beat is located, the analysis circuit module 664 removes the ectopic beat data from the motion data.

A position analysis circuit module 668 analyzes the position measurement of the heart based on at least two channels of the motion sensor. The position analysis circuit module 668 determines and locates inconsistent electrical/motion data based on the position measurements and removes the inconsistent data from the electrical/motion data.

The CPU 602 also includes a synchronization and averaging circuit module (SACM) 670. The SACM 670 receives the motion data from modules 664 and 668 and synchronizes the motion date for a corresponding map point. Once the motion data is synchronized, the SACM 670 calculates an average motion characterization waveform. The display 622 displays the average motion characterization waveform based on the calculations of the SACM 670.

The telemetry subsystem 630 includes a central processing unit (CPU) 652 in electrical communication with a telemetry circuit 654, which communicates with both an IEGM circuit 656 and an analog out circuit 658. The circuit 656 may be connected to leads 660. The circuit 656 is also connected to the implantable leads 114, 116 and 118 to receive and process IEGM cardiac signals as discussed above. Optionally, the IEGM cardiac signals sensed by the leads 114, 116 and 118 may be collected by the IMD and then transmitted, to the external device 600, wirelessly to the telemetry subsystem 630 input.

The telemetry circuit 654 is connected to a telemetry wand 662. The analog out circuit 658 includes communication circuits to communicate with analog outputs 664. The external device 600 may wirelessly communicate with the IMD and utilize protocols, such as Bluetooth, GSM, infrared wireless LANs, HIPERLAN, 3G, satellite, as well as circuit and packet data protocols, and the like. Alternatively, a hard-wired connection may be used to connect the external device 600 to the IMD.

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) are hardwired to perform the methods or portions of the methods described herein, and/or when the processors (e.g., of the devices described herein) operate according to one or more software programs that are written by one or more persons of ordinary skill in the art to perform the operations described in connection with the methods.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose several embodiments of the inventive subject matter and also to enable a person of ordinary skill in the art to practice the embodiments of the inventive subject matter, including making and using any devices or systems and performing any incorporated methods. The patentable scope of the inventive subject matter is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The foregoing description of certain embodiments of the inventive subject matter will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, processors or memories) may be implemented in a single piece of hardware (for example, a general purpose signal processor, microcontroller, random access memory, hard disk, and the like). Similarly, the programs may be stand-alone programs, may be incorporated as subroutines in an operating system, may be functions in an installed software package, and the like. The various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the inventive subject matter are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

In some embodiments, code including instructions (e.g., software, firmware, middleware, etc.) may be executed on one or more processing devices to implement one or more of the described functions or components. The code and associated components (e.g., data structures and other components used by the code or used to execute the code) may be stored in an appropriate data memory that is readable by a processing device (e.g., commonly referred to as a computer-readable medium).

The components and functions described herein may be connected or coupled in many different ways. The manner in which this is done may depend, in part, on whether and how the components are separated from the other components. In some embodiments some of the connections or couplings represented by the lead lines in the drawings may be in an integrated circuit, on a circuit board or implemented as discrete wires or in other ways.

What is claimed is:

1. A method comprising:
   acquiring, using one or more processors, data recordings of at least one of electrical sensor measurements from an electrical sensor, or motion data from a motion sensor, in contact with the region of interest;
   determining, using one or more processors, cycle lengths (CLs) associated with cardiac events in the data recordings;
   obtaining a test CL from the data recordings;
   generating a count of how many cardiac events have CLs that fall within an upper and a lower threshold of the test CL;
   identifying, using one or more processors, a reference cycle length based on the count; and
   displaying electrical and/or motion map data using a display based on the reference cycle length.

2. The method of claim 1, further comprising:
   saving the count as a proximity count;
   repeating the counting and saving operation for multiple test CLs; and
   saving the proximity counts as a proximity list, wherein identifying, using one or more processors, a reference cycle length based on the count comprises identifying a reference cycle length from the proximity list.

3. The method of claim 2, wherein the reference cycle length is the test CL having the most cardiac events within the upper and lower thresholds of the test CL.

4. The method of claim 1, further comprising choosing for analysis the cardiac event within each data recordings that has an associated CL that is within a programmed range of the reference cycle length.

5. The method of claim 1, wherein acquiring data recordings comprises collecting a base data recording over a single data recording duration, the method further comprising:
   determining the cycle length for the electrical and/or motion data collected during each cardiac event in the single data recording; and
   calculating a mean of the CLs in the base data recording to determine a base CL.

6. The method of claim 5, wherein acquiring data recordings further comprises prospectively collecting a next data recording over a next data recording duration, and wherein the method further comprises:
   measuring CLs associated with cardiac events in the next data recording duration; and
   determining whether the CL for the cardiac events in the next data recording duration are within upper and lower thresholds of the base CL.

7. The method of claim 6, wherein if a CL for a cardiac event in the next data recording duration is within an the upper and lower thresholds of the base CL, the method stops collecting the next data recording and recalculates and updates the base CL based on the current CL base and the cardiac event in the next data recording duration that is within the upper and lower thresholds of the base CL.

8. The method of claim 1, wherein acquiring data recordings further comprises prospectively collecting a next data recording over a next data recording duration, and wherein the method further comprises:
   measuring CLs associated with cardiac events in the next data recording duration; and
   determining whether the CL for the cardiac events in the next data recording duration are within upper and lower thresholds of the reference CL, wherein if a CL for a cardiac event in the next data recording duration is within an the upper and lower thresholds of the reference CL, the method stops collecting the next data recording and recalculates and updates the reference CL based on the current reference CL and the cardiac event in the next data recording duration that is within the upper and lower thresholds of the reference CL.

9. A system comprising:
   a data storage configured to record at least one of: electrical sensor measurements from an electrical sensor, or motion data from a motion sensor, in contact with a region of interest;
   a processor configured to:
   determine cycle lengths (CLs) associated with cardiac events in the data recordings;
   obtain a test CL from the data recordings;
   count how many cardiac events in the data recordings have CLs that fall within an upper and a lower threshold of the test CL; and
   identify a test CL as a reference cycle length based on the count; and
   a display configured to display electrical and/or motion map data based on the reference cycle length.

10. The system of claim 9, wherein the processor is further configured to
    save the count as a proximity count;
    repeat the counting and save operation for multiple test CLs; and
    save the proximity counts as a proximity list, wherein the processor is configured to identify the reference cycle length based on the count by identifying a reference cycle length from the proximity list.

11. The system of claim 10, the processor is configured to identify test CL having the most cardiac events within the upper and lower thresholds of the test CL as the reference cycle length.

12. The system of claim 9, wherein the processor is further configured to choose for analysis the cardiac event within each data recordings that has an associated CL that is within a programmed range of the reference cycle length.

13. The system of claim 9, wherein the data storage is further configured to record base data over a single data recording duration, and wherein the processor is further configured to:
- determine the cycle length for the electrical and/or motion data collected during each cardiac event in the single data recording; and
- calculate a mean of the CLs in the base data recording to determine a base CL.

14. The system of claim 13, the data storage is further configured to prospectively collect a next data recording over a next data recording duration, and wherein the processor is further configured to:
- measure CLs associated with cardiac events in the next data recording duration; and
- determine whether the CL for the cardiac events in the next data recording duration are within upper and lower thresholds of the base CL.

15. The system of claim 14, wherein the data storage is further configured to stop collecting the next data recording if a CL for a cardiac event in the next data recording duration is within an the upper and lower thresholds of the base CL, and the programmer is further configured to recalculate and update the base CL based on the current CL base and the cardiac event in the next data recording duration that is within the upper and lower thresholds of the base CL.

16. The system of claim 9, wherein the data storage is further configured to prospectively collect a next data recording over a next data recording duration, and wherein the programmer is further configured to:
- measure CLs associated with cardiac events in the next data recording duration; and
- recalculate and update the reference CL based on a current reference CL and cardiac events in the next data recording having duration that are within the upper and lower thresholds of the current reference CL.

* * * * *